(12) United States Patent
Duncan

(10) Patent No.: US 9,044,539 B2
(45) Date of Patent: Jun. 2, 2015

(54) IV LINE CLASP

(71) Applicant: Trenclasp LLC, Tulsa, OK (US)

(72) Inventor: Jessica L. Duncan, Colcord, OK (US)

(73) Assignee: Trenclasp, LLC, Tulsa, OK (US)

( * ) Notice: Subject to any disclaimer, the term of this patent is extended or adjusted under 35 U.S.C. 154(b) by 102 days.

(21) Appl. No.: 13/958,976

(22) Filed: Aug. 5, 2013

(65) Prior Publication Data

US 2014/0276439 A1     Sep. 18, 2014

Related U.S. Application Data

(63) Continuation-in-part of application No. 13/803,529, filed on Mar. 14, 2013, now Pat. No. 8,672,891.

(51) Int. Cl.
*A61M 5/32*   (2006.01)
*A61M 5/158*  (2006.01)
*A61M 25/02*  (2006.01)

(52) U.S. Cl.
CPC .............. *A61M 5/158* (2013.01); *A61M 25/02* (2013.01); *A61M 2025/024* (2013.01); *A61M 2025/028* (2013.01); *A61M 2025/026* (2013.01)

(58) Field of Classification Search
USPC .................................................. 604/177–180
See application file for complete search history.

(56) References Cited

U.S. PATENT DOCUMENTS

| | | | |
|---|---|---|---|
| 2,409,432 A * | 10/1946 | Hubbard ....................... 604/179 |
| 2,449,882 A * | 9/1948 | Daniels ......................... 604/179 |
| 3,160,158 A * | 12/1964 | Rayhart ......................... 604/179 |
| 3,167,072 A * | 1/1965 | Hester et al. .................. 604/179 |
| 3,782,378 A * | 1/1974 | Page .............................. 128/888 |
| 4,316,461 A * | 2/1982 | Marais et al. ................. 604/179 |
| 4,326,517 A * | 4/1982 | Whitney et al. .............. 604/155 |
| 4,453,933 A * | 6/1984 | Speaker ......................... 604/179 |
| 4,470,410 A * | 9/1984 | Elliott ............................ 128/877 |
| 4,591,356 A * | 5/1986 | Christie ......................... 604/179 |
| D290,041 S * | 5/1987 | Scott ............................. D24/128 |
| 4,898,587 A * | 2/1990 | Mera .............................. 604/174 |
| 4,919,150 A | 4/1990 | Grant |
| 5,084,026 A * | 1/1992 | Shapiro ......................... 604/179 |
| 5,131,412 A | 7/1992 | Rankin |
| 5,188,608 A * | 2/1993 | Fritts ............................. 604/179 |
| 5,190,530 A | 3/1993 | Greeff et al. |
| 5,279,574 A | 1/1994 | Forren |
| 5,344,406 A | 9/1994 | Spooner |
| 5,664,581 A * | 9/1997 | Ashley .......................... 128/876 |
| 6,000,402 A | 12/1999 | Able |
| 6,074,368 A * | 6/2000 | Wright .......................... 604/179 |
| 6,086,564 A * | 7/2000 | McLaughlin ................. 604/179 |
| 6,500,154 B1 * | 12/2002 | Hakky et al. ................. 604/174 |
| 6,526,981 B1 * | 3/2003 | Rozier et al. ................. 128/846 |

(Continued)

*Primary Examiner* — Nicholas Lucchesi
*Assistant Examiner* — Diva K Chander
(74) *Attorney, Agent, or Firm* — Molly D. McKay

(57) ABSTRACT

The present invention is an alternate IV line clasp for holding IV equipment securely to a patient's body without the use of tape. The clasp has a contoured recessed channel provided in an underside of a head of the clasp such that the channel receives and holds the IV equipment therein. The clasp has an adjustable, slightly elastic strap that extends over the head of the clasp by inserting through slits provided on either side of the head and then extending around the patient's body in the area of the body where the IV is installed. The two ends of the strap are provided, respectively, with hook and loop fasteners that allow the strap to be removably secured to itself and around the patient's body to hold the head and attached IV in place.

7 Claims, 7 Drawing Sheets

(56) References Cited

U.S. PATENT DOCUMENTS

| | | | |
|---|---|---|---|
| 7,198,616 B2* | 4/2007 | Mossanen-Shams et al. | 604/174 |
| 7,626,070 B2* | 12/2009 | Propp | 602/41 |
| 8,109,912 B2* | 2/2012 | Alferness et al. | 604/181 |
| 8,197,447 B2* | 6/2012 | Wright | 604/174 |
| 8,211,064 B2* | 7/2012 | Sloan | 604/179 |
| 8,298,191 B2* | 10/2012 | Bierman et al. | 604/180 |
| 8,500,698 B2* | 8/2013 | Kyvik et al. | 604/174 |
| 2004/0034330 A1* | 2/2004 | Bierman et al. | 604/500 |
| 2005/0131353 A1* | 6/2005 | Mossanen-Shams et al. | 604/179 |
| 2005/0137496 A1* | 6/2005 | Walsh et al. | 600/561 |
| 2009/0137962 A1* | 5/2009 | Bracken et al. | 604/179 |
| 2010/0106095 A1* | 4/2010 | Vitaris et al. | 604/177 |
| 2010/0114034 A1* | 5/2010 | Wright et al. | 604/177 |
| 2010/0179481 A1* | 7/2010 | Bierman et al. | 604/177 |
| 2010/0234804 A1* | 9/2010 | Hiejima et al. | 604/110 |
| 2014/0081211 A1* | 3/2014 | Laird | 604/179 |

* cited by examiner sides ss US 9,044,539 B2

IV LINE CLASP

CROSS-REFERENCE TO RELATED APPLICATIONS

The present application is a continuation in part of U.S. patent application Ser. No. 13/803,529 for IV Line Clasp that was filed on Mar. 14, 2013.

BACKGROUND OF THE INVENTION

1. Field of the Invention

The present invention relates to a device for holding a non-ported IV that is installed in a patient's body so that it does not move. Specifically, the invention is an IV line clasp that takes the place of tape to hold an IV line in place on the patient.

2. Description of the Related Art

The present method for holding an installed intravenous (IV) needle is to put tape or some type of elastic band around the IV and the patient's body where the IV is installed. The problem with using tape is that the IV can shift under the tape and become dislodged. A still further problem with use of tape is that the tape can cause allergic reactions, can irritate or actually cause the skin to be removed when the tape is removed from the patient's body. This is particularly problematic when the skin is delicate, such as on an infant or elderly person or where there has been damage to the skin, such as in the case of a burn patient.

Use of an elastic band around the patient's body to secure the IV is also problematic since the elastic band can cut off circulation and result in tissue damage or death of tissue, even to the point of the patient losing a limb.

The present invention addresses these problems by providing an IV line clasp that receives and holds the IV equipment securely within a contoured recess or channel provided in the head of the clasp and that has an adjustable strap attaching to the clasp that secures together on its opposite ends to hold the IV in place on the patient's body without the use of tape.

SUMMARY OF THE INVENTION

The present invention is an IV line clasp that receives and holds the IV equipment securely within a contoured recess or channel provided in the head of the clasp and that has adjustable strap attaching to the clasp that secures together on its opposite ends to hold the IV in place on the patient's body without the use of tape.

DETAILED DESCRIPTION OF THE PREFERRED EMBODIMENT

Figure 8:
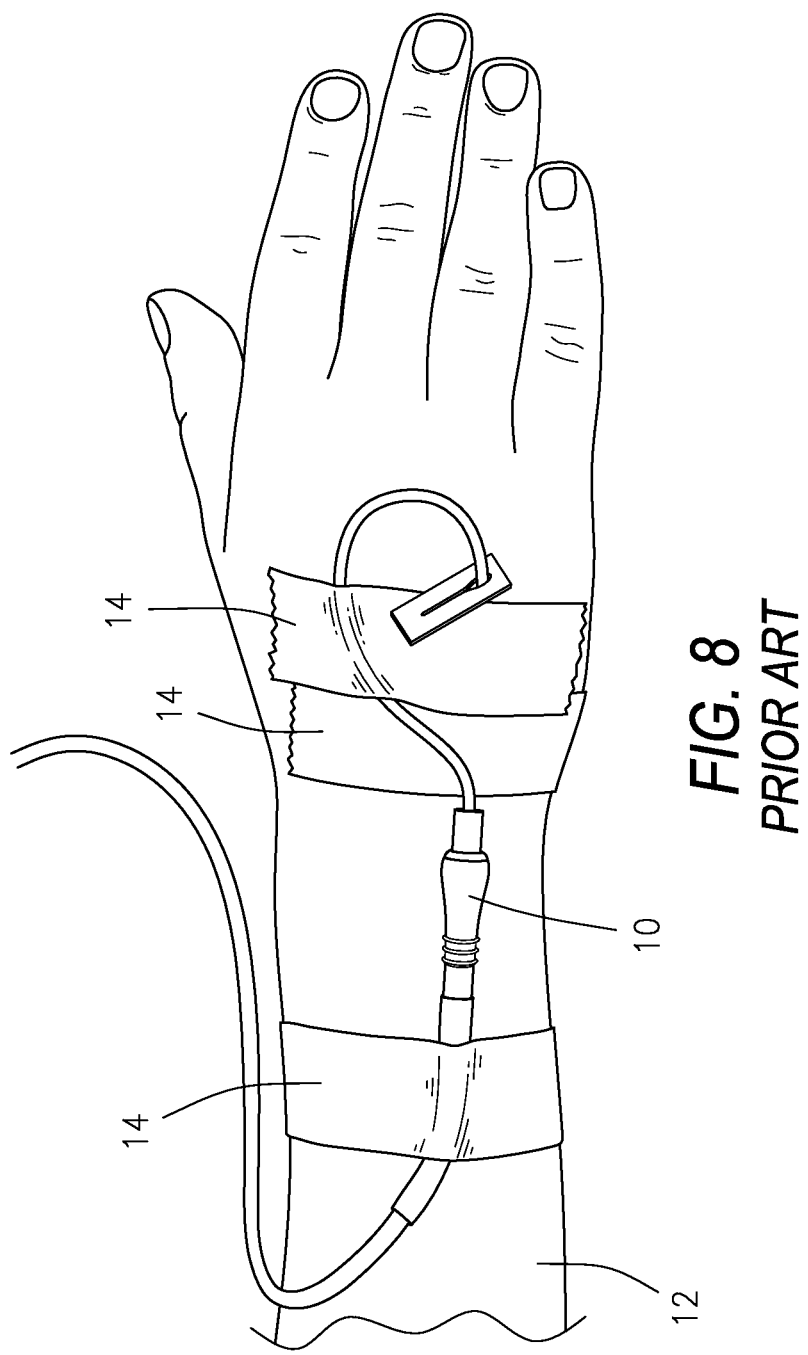
FIG. 8 is a perspective view of a prior art IV installation in the hand of a patient, showing the IV equipment secured to the patient's hand with tape.

Referring initially to FIG. 8, there is shown a typical prior art method of securing IV equipment 10 to a patient's body 12 with tape 14. It is important that the IV equipment 10 be secured to the patient's body 12 so that the IV catheter which is inserted into a vein in the patient's body 12 does not become dislodged which would require installation of a new IV catheter. However, use of tape 14 for this purpose is problematic.

Figure 1:
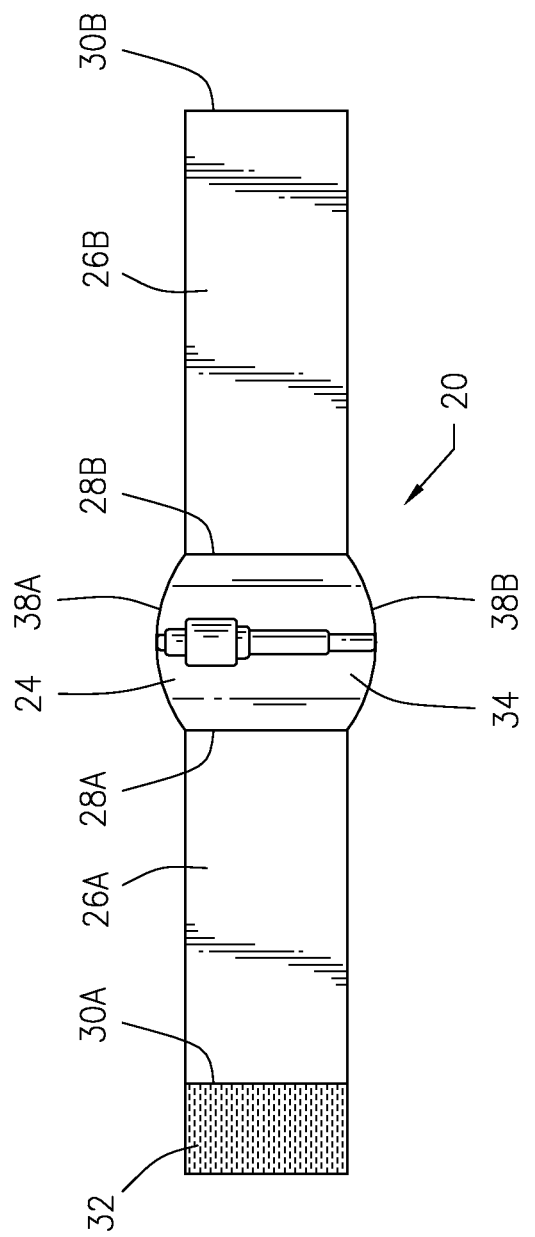
FIG. 1 is a top plan view of an IV line clasp constructed in accordance with the present invention.
Figure 2:
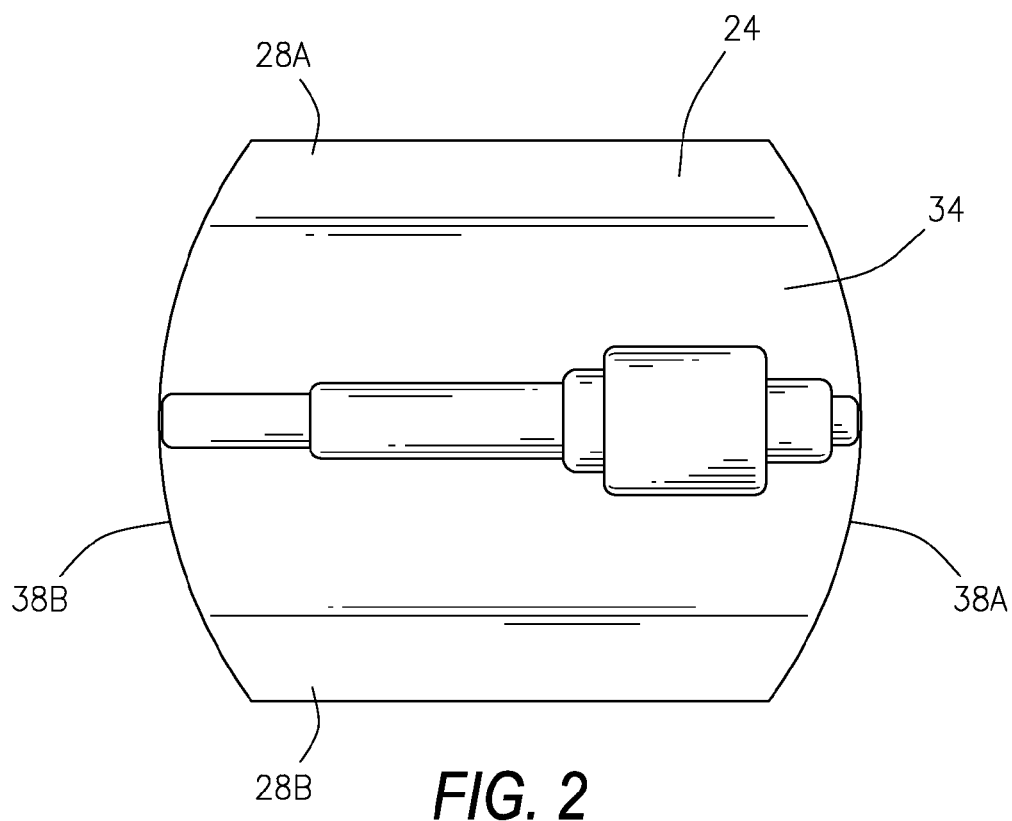
FIG. 2 is a top plan view of the head of the IV line clasp of FIG. 1, shown with the straps removed.
Figure 3:
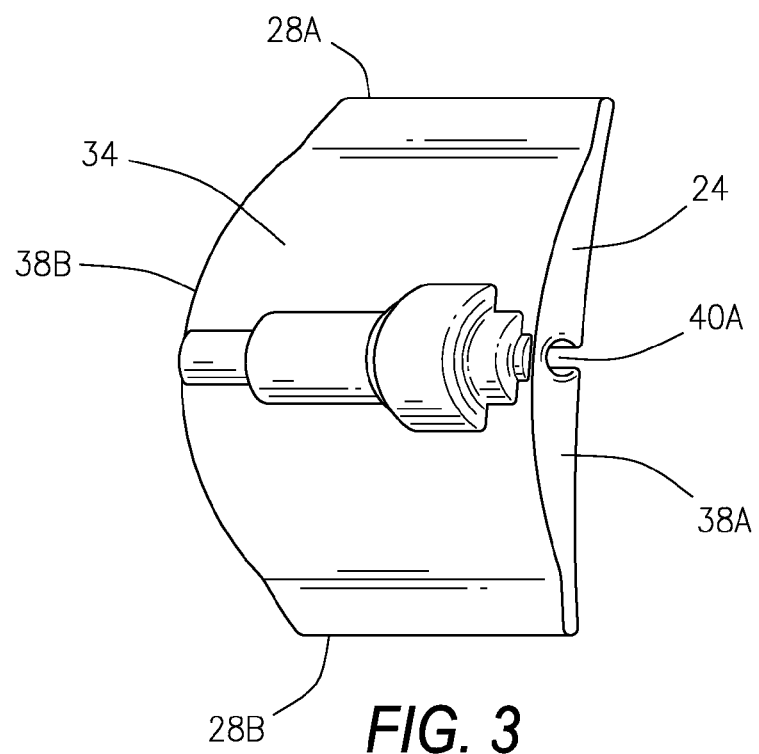
FIG. 3 is a top perspective view of the head of FIG. 2.
Figure 4:
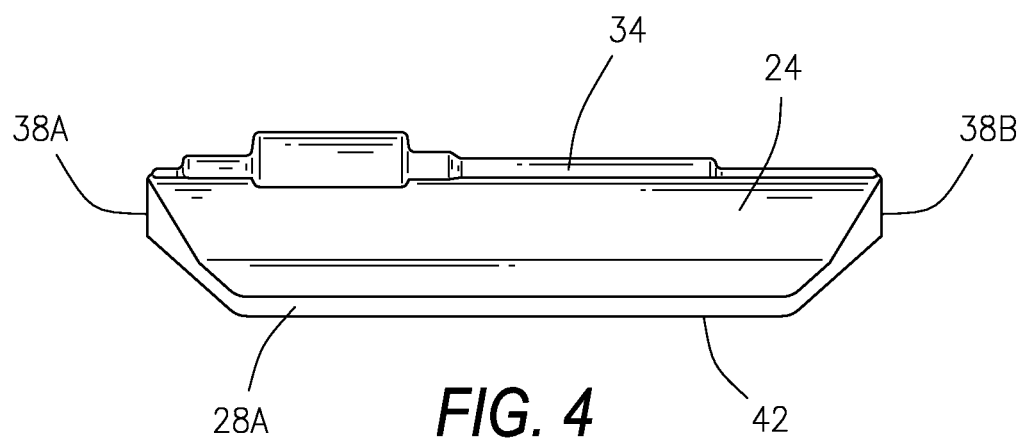
FIG. 4 is a side view of the head of FIG. 2.
Figure 5:
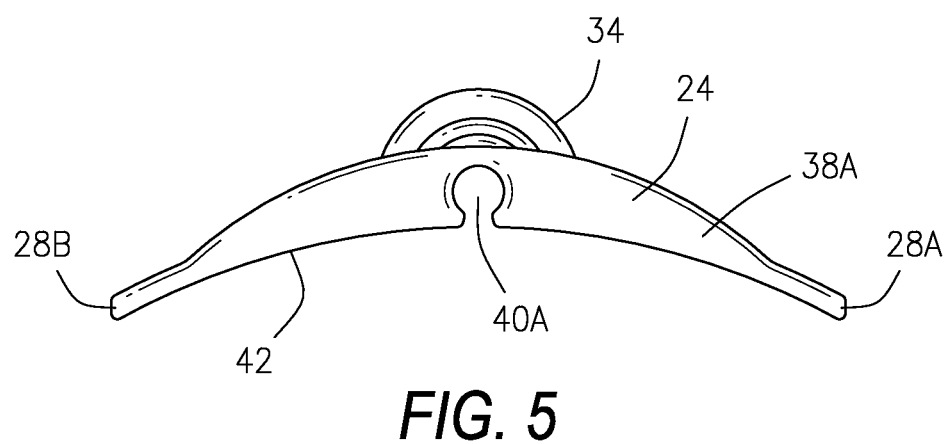
FIG. 5 is an end view of the head of FIG. 2.

Referring to FIG. 1, there is illustrated an IV line clasp 20 that is constructed in accordance with a first embodiment of the present invention. The invention is an IV line clasp 20 that receives and holds the IV equipment 10 securely within a contoured recess or channel 22 provided in a centrally located head 24 of the clasp 20. The head 24 is preferably constructed of molded plastic. Adjustable cotton straps 26A and 26B are attached on opposite ends 28A and 28B of the head 24 that secure together on distal ends 30A and 30B of the straps 26A and 26B via fasteners 32 provided on the ends 30A and 30B to hold the IV equipment 10 in place on the patient's body 12 without the use of tape 14.

The straps 26A and 26B are adjustable in length and are designed to be secured together around the patient's body 12 with fasteners 32, such as the hook and loop fastener that is illustrated. The straps 26A and 26B are preferably constructed of a comfortable, non-allergenic material that has a minimal amount of stretching capacity, such as the cotton bands that are illustrated.

FIGS. 2-7 show the detail of the head 24. The top 34 of the head 24 is arched upward and is preferably provided with a smoothly curved and contoured shape so that it is not easily snagged. The ends 28A and 28B of the head 24 are straight and approximately parallel with each other, and the straps 26A and 26B attached to the head 24 at the ends 28A and 28B. Each of the two sides 38A and 38B the head 24 is provided with a circular opening 40A and 40B. The two circular openings 40A and 40B are connected together on the underside 42 of the head 24 to form the channel 22 in which the IV equipment 10 inserts when the clasp 20 is in use, as will be more fully described hereafter.

Figure 6:
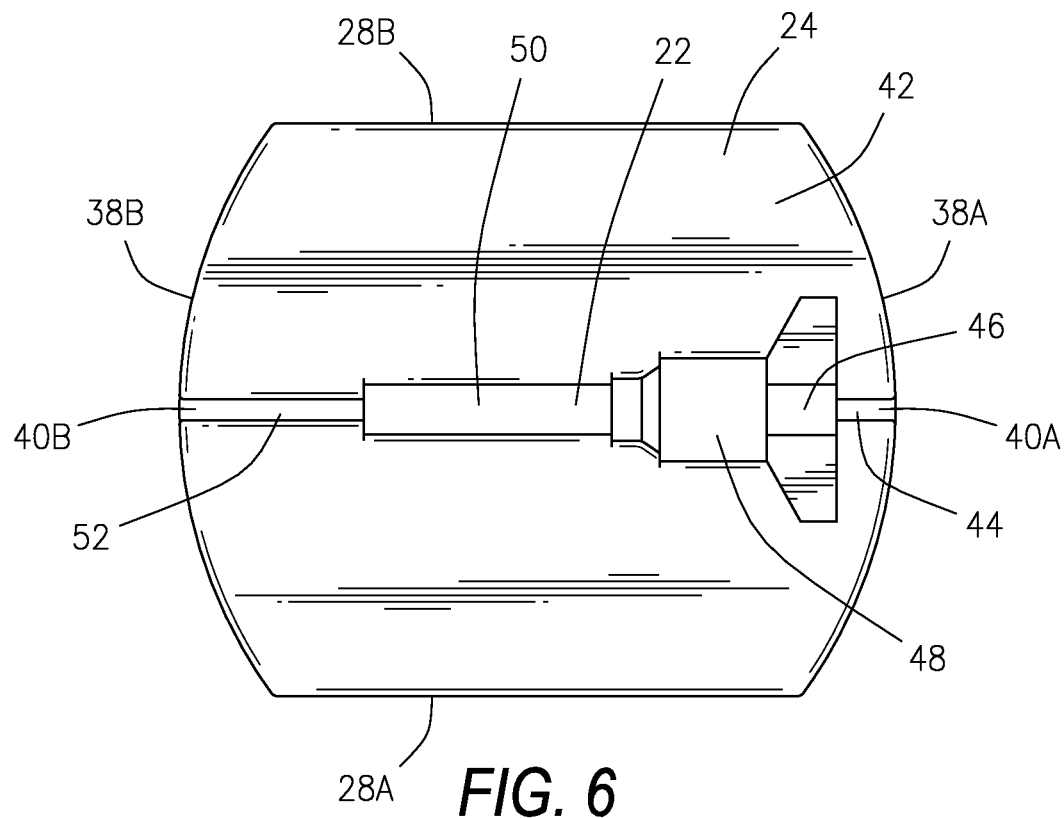
FIG. 6 is bottom plan view of the head of FIG. 2.
Figure 7:
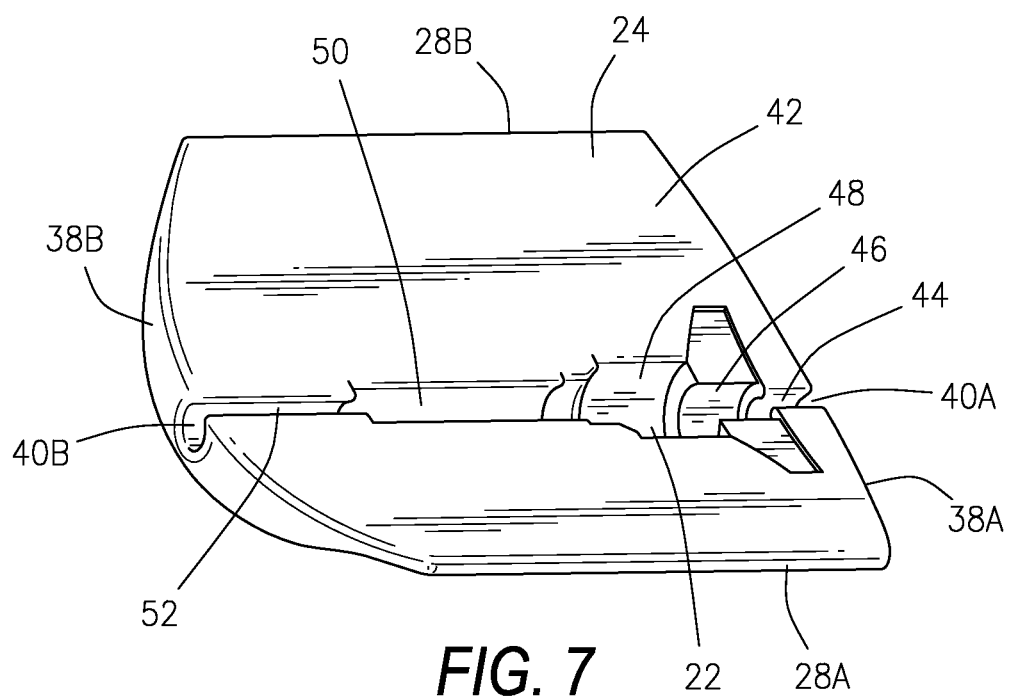
FIG. 7 is bottom perspective view of the head of FIG. 2.

Referring to FIGS. 6 and 7, the channel 22 is shaped, sized, and contoured to receive therein the IV equipment 10. Specifically, the channel 22 is provided with an IV catheter receiving section 44 that connects with the first circular opening 40A. The IV catheter receiving section 44 connects to a butterfly receiving section 46, and the butterfly receiving section 46 connects to a hub receiving section 48. The hub receiving section 48 connects to a hep lock receiving section 50, and the hep lock receiving section 50 connects to an IV line receiving section 52. The IV line receiving section 52 connects with the second circular opening 40B.

In use, the IV catheter is first installed in the patient's body 12. Then the IV line clasp 20 is placed over the IV equipment 10 so that the IV catheter of the IV equipment 10 inserts into the IV catheter receiving section 44 of the channel 22, the butterfly wings of the IV equipment 10 inserts into the butterfly receiving section 46, the hub of the IV equipment 10 inserts into hub receiving section 48, the hep lock or heparin containing lock of the IV equipment 10 inserts into the hep lock receiving section 50, and the IV line of the IV equipment 10 inserts into the IV line receiving section 52. When the IV equipment 10 is thus inserted into the channel 22, the IV catheter will exit the head 24 via the first circular opening 40A and the IV line will exit the head 24 via the second circular opening 40B. After the IV equipment 10 has been thus received in the channel 22, the straps 26A and 26B are extended around the patient's body 12 and secured together via fasteners 32 in order to secure the IV equipment 10 to the patient's body 12. The straps 26A and 26B are then adjusted in length to have a secure, but not a tight fit around the patient's body 12 so that the patient's circulation is not affected.

Figure 9:
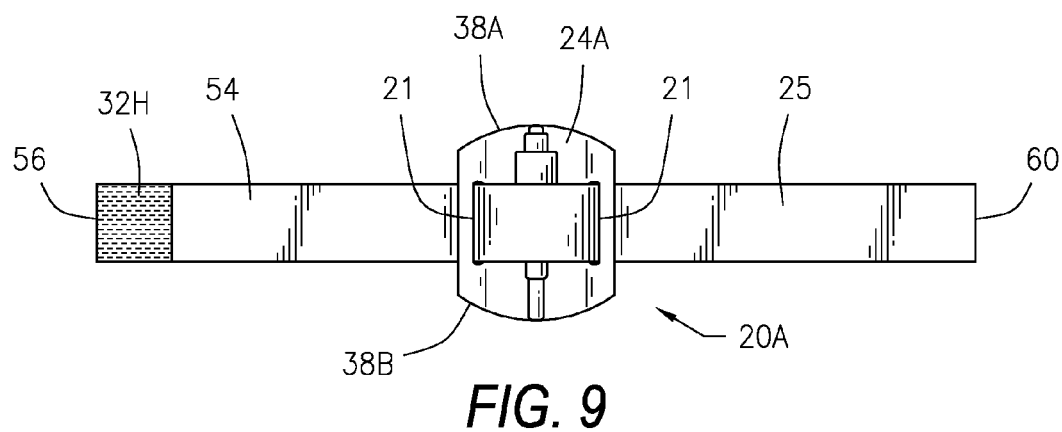
FIG. 9 is a top plan view of an alternate IV line clasp constructed in accordance with a preferred embodiment the present invention.
Figure 10:
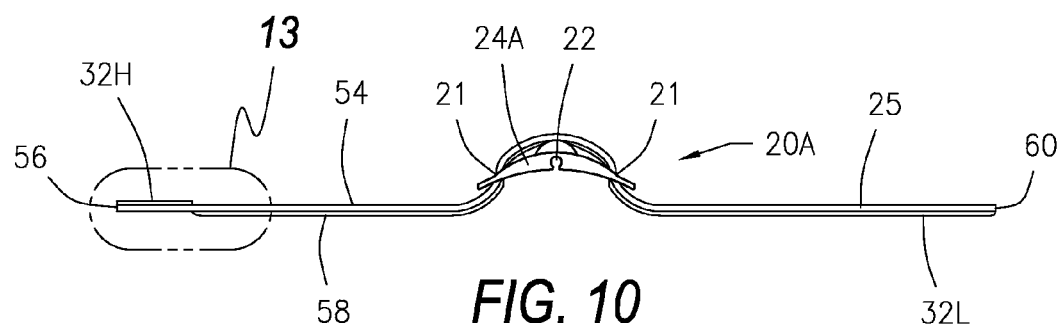
FIG. 10 is a side view of the alternate IV line clasp of FIG. 9.
Figure 12:
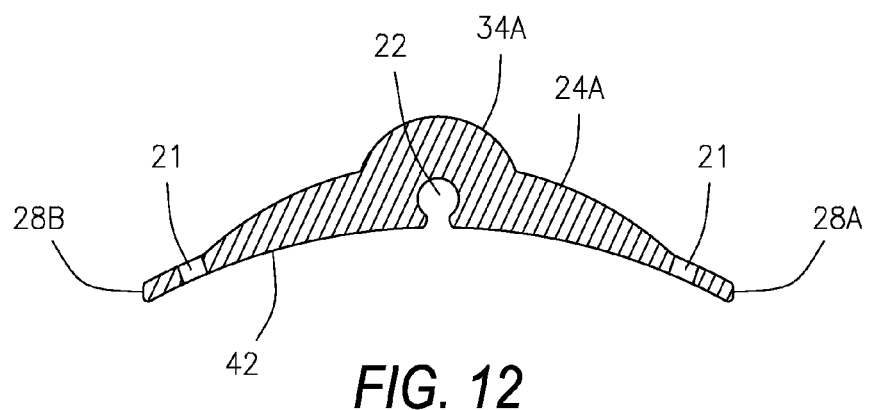
FIG. 12 is a cross sectional view taken along line 12-12 of FIG. 11.
Figure 11:
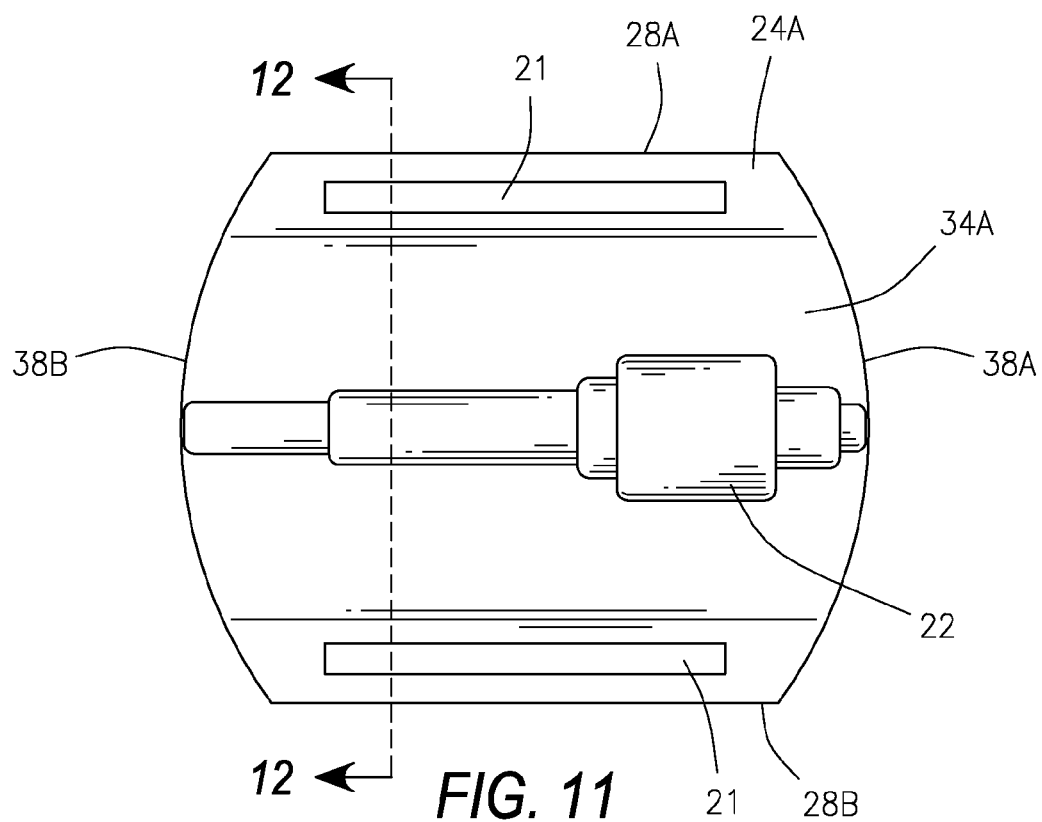
FIG. 11 an enlarged top plan view of the alternate IV line clasp of FIG. 9, shown with the strap removed.

Referring now to FIGS. 9 and 10, there is illustrated an alternate IV line clasp 20A that is constructed in accordance with a preferred embodiment of the present invention. The alternate IV line clasp 20A is substantially identical to the first IV line clasp 20 described above except that the alternate IV line clasp 20A is provided with a single strap 25 that secures the alternate head 24A of the alternate clasp 20A to the patient, as illustrated in FIGS. 9 and 10; and the alternate head 24A is modified by including a slit 21 on either side of the head 24A, as illustrated in FIGS. 11 and 12. That single strap 25 inserts through the slits 21 provided in the alternate head 24A as a means of attachment to the alternate head 24A. As illustrated in FIGS. 9 and 10, when the single strap 25 is inserted through the slits 21, the strap 25 extends over the top 34A of the alternate head 24A.

Figure 13:
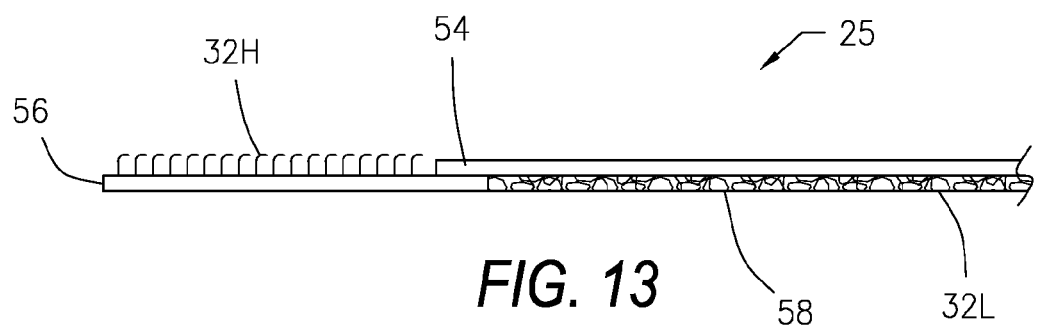
FIG. 13 is an enlarged view of the strap of the alternate IV line clasp showing the portion of the strap contained with circle 13 of FIG. 10.

Referring also to FIG. 13, the single strap 25 is provided with hooks 32H on the top side 54 of the strap 25 on a first end 56 of the strap 25 that removably engage loops 32L provided on a bottom side 58 of the strap 25 on the remaining length of the strap 25 and on an opposite second end 60 of the strap 25 as a means of attaching the single strap 25 back upon itself to form a circular band for encircling a part of the patient's body to which an IV line is to be attached, such as for example an arm of the patient. Because the hooks 32H can engage the loops 32L anywhere along the entire length of the strap 25, the circumference of a circular band created when the strap 25 attaches back upon itself is variable or adjustable to fit various sizes of parts of a patient's body to which an IV line it to be attached.

Also, it is desirable that the single strap 25 be only semi-elastic such that the strap 25 stretches slightly and clings to the patient's body when secured around the part of the patient's body to which an IV line is attached and is not easily dislodged therefrom. However, the single strap 25 should not be capable of stretching too much so that it is not so elastic that the strap 25 would present a danger of cutting off the circulation in the patient's body part to which it attaches.

The head 24A is preferably constructed of flexible plastic material that can be flexed to allow the IV equipment 10 to enter the channel 22, be held securely in the channel 22 when in use, and can be flexed to removed the IV equipment 20 from the channel 22 when desired.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. An IV line clasp for securing an IV to a patient's body without the use of tape comprising:
   a head provided with a channel for receiving IV equipment,
       an adjustable length strap that secures to the head and has ends that extend from opposite ends of the head,
       fastening means for securing distal ends of the strap to each other to secure the head to a patient's body,
   said channel is shaped and sized to receive IV equipment therein,
   said channel terminates in a first circular opening and a second circular opening provided on opposite sides of the head, and
   an IV catheter receiving section of the channel that connects to the first circular opening, the IV catheter receiving section connects to a butterfly receiving section of the channel, the butterfly receiving section connects to a hub receiving section of the channel, the hub receiving section connects to a hep lock receiving section of the channel, the hep lock receiving section connects to an IV line receiving section of the channel, and the IV line receiving section connects with the second circular opening.

2. An IV line clasp according to claim 1 wherein the first circular opening is sized to allow an IV catheter to enter the channel on one side of the head, and the second circular opening is sized to allow an IV line to enter the channel on an opposite side of the head.

3. An IV line clasp according to claim 1 wherein the fastening means is a hook and loop type fastener provided on opposite ends of the strap.

4. An IV line clasp according to claim 1 wherein the strap is somewhat elastic such that it has the ability to cling to the patient's body when in use.

5. An IV line clasp according to claim 1 wherein a top of the head is smoothly curved and contoured so it is not easily snagged.

6. An IV line clasp according to claim 1 wherein the channel is provided in the underside of the head.

7. An IV line clasp according to claim 1 wherein the head is constructed of flexible plastic material.

* * * * *